(12) United States Patent
Boutoussov et al.

(10) Patent No.: US 7,461,982 B2
(45) Date of Patent: Dec. 9, 2008

(54) CONTRA-ANGLE ROTATING HANDPIECE HAVING TACTILE-FEEDBACK TIP FERRULE

(75) Inventors: Dmitri Boutoussov, Dana Point, CA (US); Jeffrey W. Jones, Robertson, WY (US); Ioana M. Rizoiu, San Clemente, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 11/904,677

(22) Filed: Sep. 27, 2007

(65) Prior Publication Data
US 2008/0025671 A1   Jan. 31, 2008

Related U.S. Application Data

(62) Division of application No. 11/186,619, filed on Jul. 20, 2005, now Pat. No. 7,292,759.

(60) Provisional application No. 60/589,536, filed on Jul. 20, 2004.

(51) Int. Cl.
  G02B 6/36 (2006.01)
  G02B 6/04 (2006.01)
  G02B 6/06 (2006.01)
  A61B 18/18 (2006.01)
  A61B 18/22 (2006.01)

(52) U.S. Cl. .................. 385/80; 385/115; 385/119; 606/16

(58) Field of Classification Search .............. None
See application file for complete search history.

(56) References Cited

U.S. PATENT DOCUMENTS

| 5,741,247 | A | * | 4/1998 | Rizoiu et al. ............... 606/10 |
| 5,825,958 | A | | 10/1998 | Gollihar et al. |
| 6,006,001 | A | * | 12/1999 | Alfano et al. ............ 385/115 |
| 6,118,521 | A | | 9/2000 | Jung et al. |
| 6,389,193 | B1 | | 5/2002 | Kimmel et al. |

FOREIGN PATENT DOCUMENTS

JP    2003001465 A    1/2003

OTHER PUBLICATIONS

Partial English Translation for Publication No. 2003-001465, Aug. 1, 2003, [online], [retrieved on Mar. 9, 2007]. Retrieved from the Industrial Property Digital Library of the Japan Patent Office using internet <URL: http://www19.ipdl.ncipi.go.jp/PA1/cgi-bin/PA1INDEX>.

* cited by examiner

*Primary Examiner*—Omar Rojas
(74) *Attorney, Agent, or Firm*—Stout, Uxa, Buyan & Mullins LLP (57) ABSTRACT

An illumination device is described containing optical fibers that transmit electromagnetic energy from a source to a target. Additional optical fibers return reflected electromagnetic energy from the target. High-level electromagnetic energy can be used for cutting, reforming, or treating a surface. Low-level electromagnetic energy illuminates the surface.

32 Claims, 4 Drawing Sheets

CONTRA-ANGLE ROTATING HANDPIECE HAVING TACTILE-FEEDBACK TIP FERRULE

CROSS-REFERENCE TO RELATED APPLICATIONS

This application is a divisional of U.S. application Ser. No. 11/186,619, filed Jul. 20, 2005 and entitled ONTRA-ANGLE ROTATING HANDPIECE HAVING TACTILE-FEEDBACK TIP FERRUL, now U.S. Pat. No. 7,292,759, the entire contents of which are incorporated herein by reference. U.S. application Ser. No. 11/186,619 claims the benefit of U.S. Provisional Application No. 60/589,536, filed Jul. 20, 2004 and entitled CONTRA-ANGLE ROTATING HANDPIECE HAVING TACTILE-FEEDBACK TIP FERRULE. This application is related to U.S. application Ser. No. 11/033,031, filed Jan. 10, 2005 and entitled HANDPIECE HAVING ILLUMINATION AND LASER OUTPUTS.

BACKGROUND OF THE INVENTION

1. Field of the Invention

The present invention relates generally to electromagnetic energy devices and, more particularly, to cutting, treatment and illumination devices that transmit electromagnetic energy toward target surfaces.

2. Description of Related Art

Electromagnetic energy devices are employed in a variety of applications. For example, a simple incandescent light may be used to illuminate an area with electromagnetic energy in a form of visible light. Another form of electromagnetic energy, such as a laser beam, may be used to illuminate an area, to identify a target, or to deliver concentrated energy to a target in order to perform various procedures such as melting, cutting, or the like.

Certain medical devices may deliver electromagnetic energy to a target surface such as, for example, an eye, in order to correct a deficiency in visual acuity. Other medical devices may direct electromagnetic energy toward a surface of a tooth to perform, for example, a cutting operation. Endoscopic devices can be used to enhance visualization of internal parts of, for example, a human body in order to detect and/or remove diseased tissue. Constructions of these devices may vary, while underlying functionalities or goals, including, for example, the provision of efficient operation by supplying optimal illumination without obstructing a user's access or view and/or the provision of reliable operation to ensure reproducibility and favorable procedural results, are often shared.

A need exists in the prior art to efficiently and reliably transmit various types of electromagnetic energy to and from target surfaces in order, for example, to enhance visualization and treatments of the target surfaces.

SUMMARY OF THE INVENTION

The present invention addresses this need by providing an illumination device that utilizes optical fibers to transmit electromagnetic energy toward a target surface. As used herein, "optical fiber" refers to any electromagnetic energy (e.g., light) transmitting medium (e.g., fiber) that is able to transmit light from one end of the fiber to another end of the fiber. The light transmission may be passive or it may include one or more light altering elements to influence the way light is emitted from the optical fiber. Optical fibers can be used to transmit any type of light, including visible light, infrared light, blue light, laser light, and the like. Optical fibers may be hollow or solid, and may include one or more reflectors within bodies of the fibers to control transmission and emission of light from the optical fibers.

An illumination device in accordance with the present invention includes a unitary distal end (output portion) and a split proximal end (input portion). As used herein, "distal end" refers to an end of an illumination device that is closest to a target surface, and "proximal end" refers to an end of an illumination device that is closest to a power source or other source of electromagnetic energy. The illumination device can include a plurality of different sized optical fibers depending on a particular application for which the illumination device is utilized. In illustrative embodiments, and as disclosed herein, the proximal end of the illumination device includes three proximal end members configured to accommodate three sets of optical fibers.

Another illumination device in accordance with the present invention includes a plurality of sets of optical fibers configured to emit electromagnetic energy from the distal end of the illumination device toward a target surface. The device further may include at least one optical fiber configured to receive electromagnetic energy from the target surface and transmit the energy to the proximal end of the illumination device. The electromagnetic energy transmitted to the proximal end of the illumination device can be used as a signal for further analysis.

In another embodiment of the present invention, an illumination device includes a handpiece having a reflector. The reflector is constructed to reflect both laser energy, such as light provided by an erbium laser, and visible light, such as blue light, toward a target surface. In an illustrated embodiment, as disclosed herein, the reflector includes a plurality of mirrors to provide enhanced control of the emission of electromagnetic energy from the optical fibers toward a target surface and of the transmission of electromagnetic energy reflected from the target surface back through the illumination device in the opposite direction.

While apparatuses and methods of the present invention have or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE INVENTION

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be utilized in conjunction with, for example, various medical and/or dental procedures that are conventionally used in the art.

Figure 1:
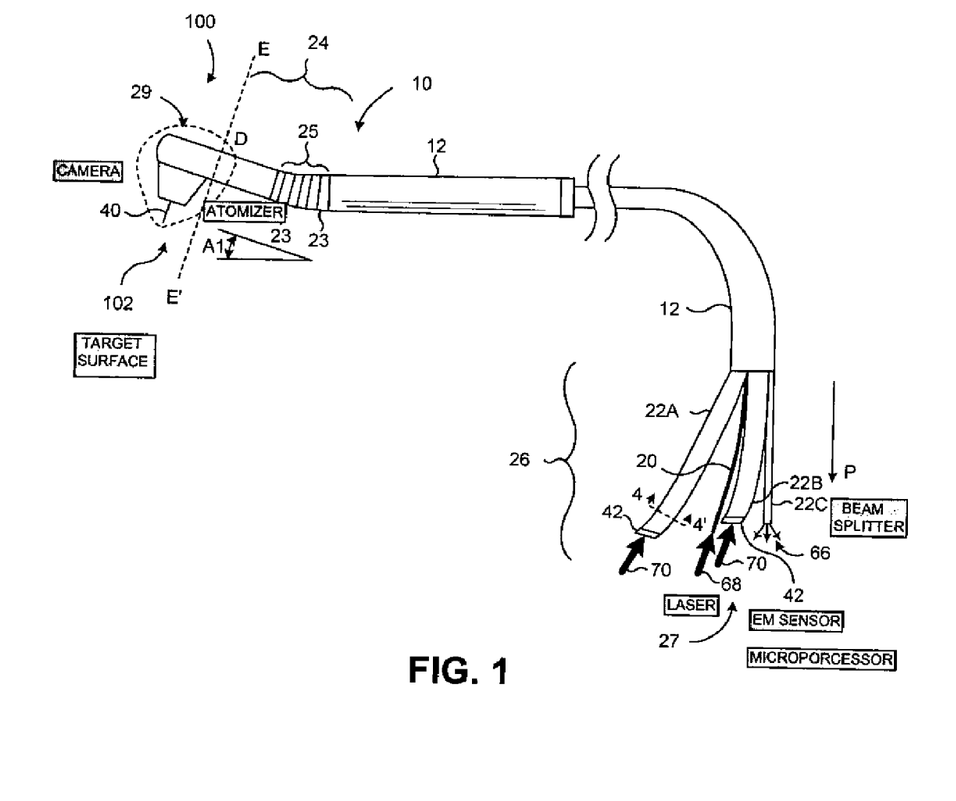
FIG. 1 is a side elevation view of an apparatus according to an example of the present invention.

Referring to the figures, and specifically FIG. 1, an apparatus comprising an illumination device 10 is illustrated. As presently embodied, illumination device 10 includes an elongate body 12 having a generally tube-like structure that is constructed to contain a plurality of light transmitters, such as optical fibers and the like, which are used to transmit light to and/or from a handpiece 100 (i.e., a portion of the illumination device 10 disposed distally from phantom line E-E' in FIG. 1). In the illustrated embodiment, the elongate body 12 surrounds and defines a hollow interior, such as lumen 14 (FIG. 3, infra) as is more particularly described below. Illumination device 10 has a distal end D and a proximal end P, the distal end being the end closer to an end that is normally held by a user. Referring to the illustrated embodiment, a distal portion 24 of illumination device 10 includes distal end D, and a proximal portion 26 includes proximal end P.

Elongate body 12 can comprise, for example, a hollow structure having one portion that is flexible, and a distally-disposed portion that may be substantially inflexible. With continuing reference to the illumination device 10 of FIG. 1, a fraction of distal portion 24 is substantially inflexible, or is generally rigid and straight, and a fraction 25 of elongate body 12 is flexible. Corresponding structures can be found in FIGS. 6a and 6b of U.S. Pat. No. 6,389,193, the entire contents of which are incorporated herein by reference. In the illustrated embodiment of the present invention, fixed ribs or joints 23 indicate the flexible portion of the elongate body 12. In additional embodiments, parts or all of either the length between and including distal portion 24 and proximal portion 26 are flexible. Elongate body 12 can be made from any suitable material or materials, such as stainless steel, metal coil or plastic. As presently embodied, while being flexible, the flexible portion of elongate body 12 is set to form in a neutral position an angle A1 of about 15 to 20 degrees, thereby disposing the fraction of distal portion in a contra-angle orientation relative to a part of the elongate body 12 adjacent to and proximal of the flexible portion. In a modified embodiment, a jointed section formed by joints 23 forms the same angle but is not flexible (i.e., is rigid) or is substantially non-flexible. While the illumination device 10 in FIG. 1 is illustrated as having a generally cylindrical cross-section, the illumination device 10 could also include one or more portions with different cross-sectional shapes including, for example, oval, rectangular, or triangular, and the like.

Figures 2, 2A:
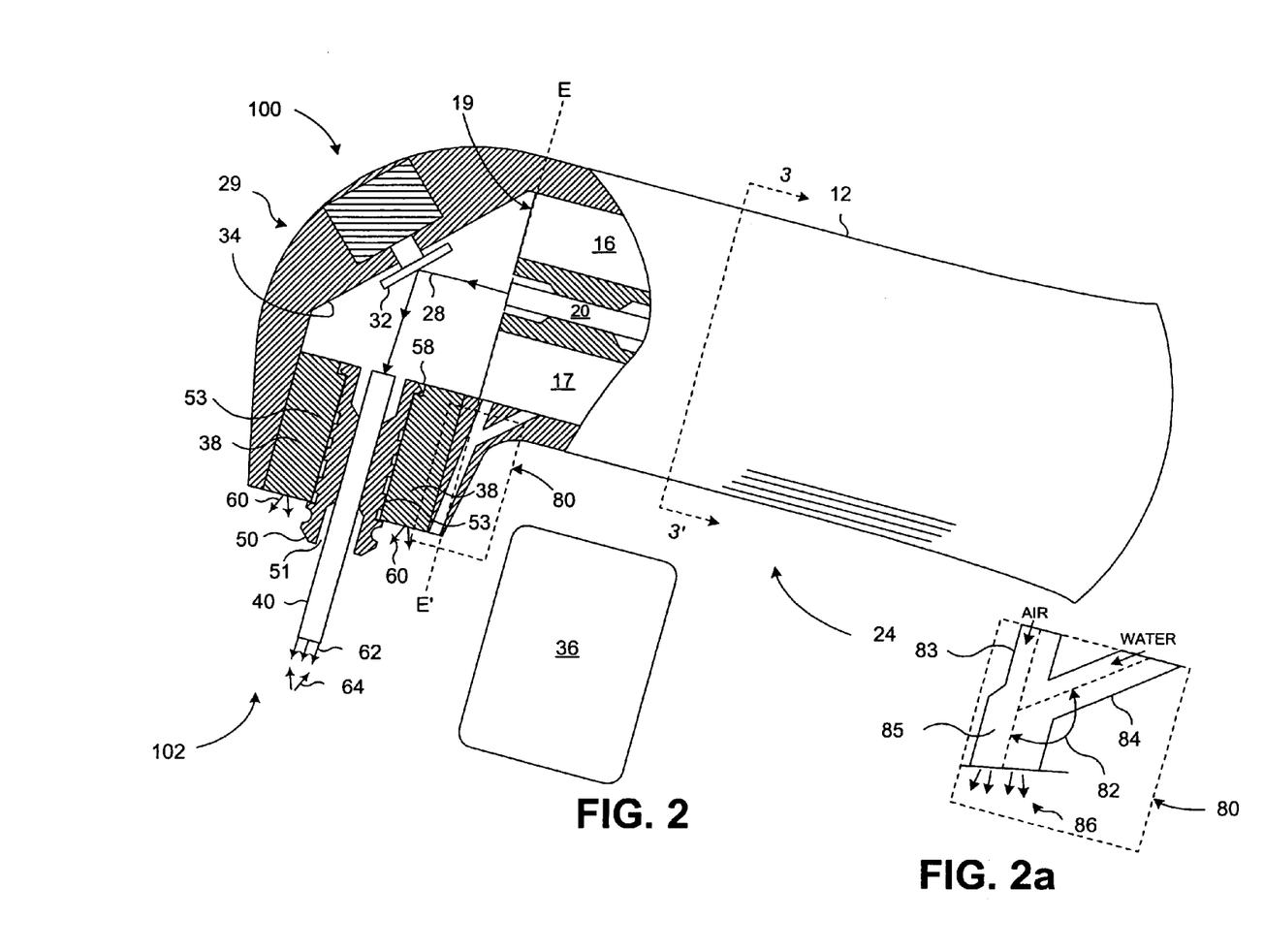
FIG. 2 is a partial cut-away diagram of a portion of the apparatus illustrated in FIG. 1.
FIG. 2a is an enlarged diagram of part of the portion illustrated in FIG. 2 depicting a mixing chamber for spray air and spray water.

The illustrated illumination device 10 comprises an output portion 29 located distally of phantom line E-E' in FIG. 1 that may be rotatable about a longitudinal axis of the distal portion 24. In modified embodiments, the output portion 29 may be only partially rotatable or entirely fixed relative to a distal end of distal portion 24. As presently embodied, the portion 29 can be rotated 360 degrees about the longitudinal axis of the distal portion 24. Referring to FIG. 2, it may be noted that a first reflector or mirror 32 and a second reflector or mirror 34 can operate to maintain an accurate coupling between output ends of fibers of the distal portion 24 and input ends of a sleeve 38 and tip 40 (e.g., a fiber tip) independent of any rotational orientation of output portion 29, thereby resulting in a handpiece 100 that can be, in some embodiments, a 360-degree fully rotating instrument. As illustrated, the handpiece 100, which may be constructed of lightweight (i.e. low mass) materials such as exhibits, in some embodiments, a contra-angle design constructed to provide relatively high maneuverability and/or visibility of a working surface (e.g., a surgical field). The design further can feature a reduced profile when compared with conventional handpieces, thereby minimizing view-obstruction, which may be caused by other handpieces during procedures. When employed in medical applications such as dental applications, these characteristics of the present invention may produce enhanced patient and user comfort and, further, may provide improved efficiency, accuracy, and access to areas of for example an oral cavity. The sleeve 38 and tip 40 are described below with reference to FIGS. 2, 5 and 6. U.S. Pat. No. 6,389,193, describes an embodiment of a rotating handpiece that may be incorporated into the present invention to the extent compatible or modifiable by one skilled in the art to be compatible and not mutually exclusive. Additionally, other embodiments may be modified by one skilled in the art to be compatible and then incorporated into the present invention.

Illumination device 10 is illustrated having a plurality of proximal members 22A, 22B, and 22C. Proximal members 22A, 22B, and 22C have hollow interiors configured to accommodate one or more light transmitters or other tubular or elongate structures having cross-sectional areas less than the cross-sectional areas of the respective hollow interiors. Proximal members 22A, 22B, and 22C are arranged such that the hollow interiors of each of the proximal members is in communication with the lumen 14 (FIG. 3) of elongate body 12. This arrangement provides for a substantially continuous path for the light transmitters to extend from proximal end P to distal end D of elongate body 12. Although the illustrated embodiment is provided with three proximal members, additional embodiments could be provided with two, or four or more proximal members, depending on, for example, a number of light transmitters being used in the illumination device 10. In addition, the illustrated embodiment of illumination device 10 includes two proximal members 22A and 22B that have substantially equal diameters, and one proximal member 22C that has a diameter that is less than either of the diameters of the other two proximal members.

Illumination device 10 is illustrated as being configured to be held by a user. In an exemplary embodiment, illumination device 10 is configured to direct electromagnetic energy from or in conjunction with the output portion 29 of handpiece 100 and/or to receive energy that may be generated (e.g., reflected from a target) in proximity to the handpiece 100. The illumination device 10 can be used in medical, industrial, dental, and other applications. In one embodiment, the illumination device 10 is a device for emitting electromagnetic energy in dental applications. The electromagnetic energy preferably includes light, such as visible light, laser light (e.g., infrared laser light) and the like. The device can be used, for example, in dental hygiene procedures.

Illumination device 10 is typically connected to at least one external electromagnetic energy source, such as a laser and/or one or more light emitting diodes (LEDs), and/or (in alternative embodiments) a lamp, so that electromagnetic energy generated by the electromagnetic energy source can be transmitted through illumination device 10 to the handpiece 100 and directed from the handpiece 100 to a target (e.g., a treatment surface such as a tooth). In modified embodiments, the electromagnetic energy source and/or other components may comprise parts or substantially all of that described in U.S. Pat. No. 5,741,247 to the extent compatible or modifiable by one skilled in the art to be compatible and not mutually exclusive. Moreover, in other embodiments wherein fluid outputs and fluids (e.g., fluid outputs and fluids as described in U.S. Pat. No. 5,741,247) are implemented, the fluid outputs and fluids may comprise parts or substantially all of any of that described in U.S. application Ser. No. 11/042,824, filed Jan. 24, 2005 and entitled ELECTROMAGNETICALLY INDUCED TREATMENT DEVICES AND METHODS, to the extent compatible or modifiable by one skilled in the art to be compatible and not mutually exclusive.

Distal portion 24 of the illumination device 10 of FIG. 1 can comprise, as presently embodied, a unitary structure having an inner lumen 14 (FIG. 3) forming a distal portion tube. Proximal members 22A, 22B, and 22C of the proximal portion 26 can each have, in an exemplary embodiment, a lumen in communication with the lumen 14 of distal portion 24. Referring to elongate body 12 of FIG. 1, in an exemplary implementation proximal members 22A, 22B, and 22C can be integrally formed with distal portion 24 of the elongate body 12. In additional embodiments, one or more proximal members may comprise separate elements that are joined or connected to elongate body 12 so that the proximal member lumens are in communication with the hollow interior or lumen 14 of distal portion 24.

In a representative embodiment of elongate body 12, distal end D includes an electromagnetic energy emitting internal output end 19 that, as presently embodied, coincides with phantom line E-E', and proximal end P includes an electromagnetic energy input end 27 (FIG. 1). Referring to proximal members 22A, 22B, and 22C of FIG. 1, each proximal member can include a lumen dimensioned to accommodate one or more light transmitters or other tube- or fiber-like structures. In the illustrated embodiment, proximal members 22A and 22B each contain three energy-emitting fibers, such as optical fibers, and proximal member 22C can contain six energy-emitting fibers, such as optical fibers. In certain implementations, as a result of proximal member 22C being illustrated as having a smaller cross-sectional area relative to proximal members 22A and 22B, the cross-sectional area of each of the optical fibers (e.g., one, three, or six fibers) in proximal member 22C can be less than cross-sectional areas of the optical fibers in proximal members 22A and 22B. As illustrated in the embodiment of FIG. 4, which is a cross-sectional view along line 4-4' of FIG. 1, the proximal member 22A can comprise three optical fibers 16 that can be substantially fused together to define a unitary light emitting assembly or waveguide. In modified embodiments, the three optical fibers 16 may be joined by other means or not joined. A structure similar to that of FIG. 4 may describe proximal member 22B, which may be similarly formed of fibers designated by reference numeral 17 in FIG. 3, which is a cross-sectional view taken along line 3-3' of FIG. 2 near distal end D of elongate body 12. Proximal member 22C can include six relatively small fibers 18, as likewise is shown in the cross-sectional view of FIG. 3. Fibers 18 are illustrated as being separate from each other, but in additional embodiments, two or more of the fibers 18 can be fused or otherwise joined together at or near one or more of the proximal end P and the distal end D. Fibers 16, 17 and 18 can be manufactured from plastic using conventional techniques, such as extrusion and the like.

Figure 3:
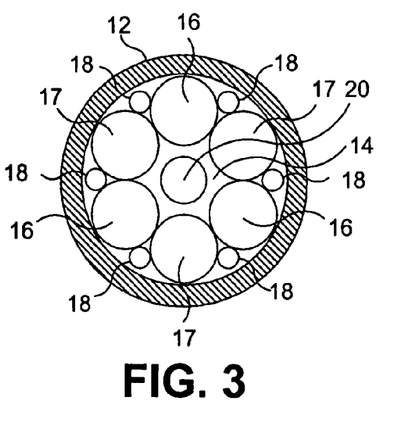
FIG. 3 is a cross-sectional view taken along line 3-3' of FIG. 2.
Figure 4:
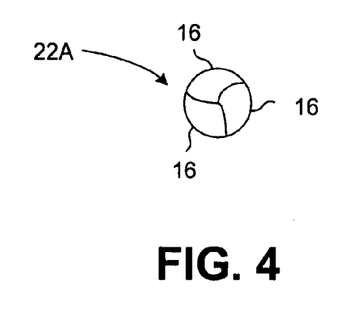
FIG. 4 is a cross-sectional view of a proximal member taken along line 4-4' of FIG. 1.

Another optical fiber 20 is illustrated in FIG. 1, passing between proximal members 22A and 22B near the input end 27 of elongate body 12, and being centrally disposed relative to fibers 16, 17 and 18 near the internal output end 19 (FIG. 2) of elongate body 12 as shown in FIG. 3. Optical fiber 20 is illustrated as a power erbium fiber that is structured to fit inside elongate body 12, although optical fiber 20 may comprise other structures in modified embodiments. As partially shown in FIG. 2, fibers 16, 17, 18 and 20 may terminate at the internal output end 19 (FIG. 2) located inside the elongate body 12. At the internal output end 19 (FIG. 2), the fibers 16, 17, 18, and 20 can be arranged in a plane to form a planar surface. In an example, the fibers can be cut and polished in the same plane and arranged to be maintained in a substantially fixed position relative to one another and the handpiece 100. For example, tubing, such as metal tubing, can be used both at the inside of elongate body 12 and outside of elongate body 12 to keep part, and preferably all, of the fibers 16, 17, 18 and 20 in a fixed, straight position.

At the input end 27, or proximal end P as illustrated in FIG. 1, fibers 16 and 17 of respective proximal members 22A and 22B are configured to receive and transmit light from, for example, a laser and/or an LED, and/or, in alternative embodiments, a lamp. As presently embodied, blue light 70, for example blue light generated by one or more blue light LEDs, is received by proximal members 22A and 22B. In the illustrated embodiment, two blue light LEDs are used as a source of blue light for transmission through fibers 16 and 17, each LED generating, for example, electromagnetic energy at a wavelength of about 470 nanometers (nm) and a power level of about 200 milliwatts (mW) either in a continuous wave (CW) or pulsed mode. Blue light can be particularly useful in curing dental composites, whitening teeth, and detecting caries, among other things, when the illumination device 10 is used for dental care and hygiene. Each of the proximal members 22A and 22B is illustrated as including an optional light altering element such as, for example, a shutter mechanism or filter 42 to influence, for example, the transmission of blue light from the LEDs. In the illustrated embodiment, each shutter mechanism or filter 42 is structured to convert blue light into white, or any other visible light. This conversion may be accomplished by using or placing phosphoric filters in front of each of the proximal members 22A and 22B.

Proximal member 22C is configured to accommodate the six smaller optical fibers 18, as described above. In the illustrated embodiment, optical fibers 18 are configured to collect or receive reflected and scattered light 64 (FIG. 2) from a treatment output end 102 of handpiece 100 and to guide the reflected and scattered light 64 back toward the input end 27 (FIG. 1). The reflected and/or scattered light can be used as a feedback signal 66, which can be passed to a sensor or other suitable device for analysis. The feedback signal 66 may be used, for example, by a microprocessor, to detect damage of an optical surface (e.g., a red light beam used for aiming may scatter and reflect back) or fluorescence of dental material (e.g., caries, bacteria, demineralization, and the like), among other things. Use of the feedback signal 66 in detection of dental caries is described in co-pending U.S. Provisional Application No. 60/601,437, filed Aug. 12, 2004 and entitled CARIES DETECTION USING TIMING DIFFERENTAILS BETWEEN EXCITATION AND RETURN PULSES.

The optical fiber 20, which may be an erbium fiber or other suitable laser emitting fiber, can be inserted into elongate body 12 such that a distal end of optical fiber 20 is co-planar (cf. plane coincident with phantom line E-E' of FIG. 2) with fibers 16, 17 and 18 at distal end D of illumination device 10. In the illustrated embodiment, optical fiber 20 is centrally disposed along a central longitudinal axis of elongate body 12, as shown in FIGS. 2 and 3. In the illustrated configuration, fibers 16, 17 and 18 are perimetrically disposed around optical fiber 20, at least at the distal end D of illumination device 10. The concentric configuration of fibers 16, 17, 18 and 20 can be maintained for any desired distance of elongate body 12. In the illustrated embodiment, the concentric configuration is maintained until a region, (e.g., proximal portion 26) where proximal members 22A, 22B, and 22C split from elongate body 12.

At the treatment output end 102 (FIG. 2), light is emitted from and collected into the handpiece 100. In the illustrated embodiment, light or other electromagnetic radiation is emitted from one or more of the fibers 16 and 17 at the internal output end 19 (FIG. 2), and light is collected by fibers 18. In addition, light or other electromagnetic radiation from a laser, and/or an LED, and/or a lamp, can be emitted from optical fiber 20. In an illustrative embodiment, electromagnetic radiation 68 (FIG. 1) is derived from an erbium, chromium, yttrium scandium gallium garnet (Er, Cr:YSGG) solid state laser, which generates electromagnetic energy having a wavelength of approximately 2.78 microns at an average power of about 6 watts (W), a repetition rate of about 20 hertz, and a pulse width of about 150 microseconds. Moreover, electromagnetic radiation 68 may further comprise an aiming beam, such as light having a wavelength of about 655 nm and an average power of about 1 mW emitted in a continuous-wave (CW) mode. In one embodiment, blue and white light are emitted from one or more of the fibers 16 and 17 toward a working surface, reflected light from the working surface is collected by fibers 18, and erbium laser light is emitted from optical fiber 20. According to another embodiment, fibers 16, for example, may emit blue light and fibers 17 may emit white light. In other embodiments, appropriate light can be emitted by one or more of the fibers 16 and 17, causing reflected white light and/or stimulated fluorescent light to be collected by fibers 18. In the above implementations, for example, the emitted light may be directed toward a working surface, such as a tissue surface, including a surface of a tooth, to perform one or more light sensitive procedures.

The present invention contemplates constructions and uses of visual feedback implements (e.g., cameras) as described in, for example, U.S. Provisional Application No. 60/688,109, filed Jun. 6, 2005 and entitled ELECTROMAGNETIC RADIATION EMITTING TOOTHBRUSH AND DENTIFRICE SYSTEM, and U.S. Provisional Application No. 60/687,991, filed Jun. 6, 2005 and entitled METHODS FOR TREATING EYE CONDITIONS, on (e.g., attached) or in a vicinity of (e.g., on or near, attached or not, output ends) of electromagnetic energy output devices (e.g., lasers and dental lasers), wherein such output devices, constructions and uses can be, in whole or in part, including any associated methods, modifications, combinations, permutations, and alterations of any constructions(s) or use(s) described or referenced herein or recognizable as included or includable in view of that described or referenced herein by one skilled in the art, to the extent not mutually exclusive, as described in U.S. application Ser. No. 11/033,032, filed Jan. 10, 2005 and entitled ELECTROMAGNETIC ENERGY DISTRIBUTIONS FOR ELECTROMAGNETICALLY INDUCED DISRUPTIVE CUTTING, U.S. application Ser. No. 11/033,043, filed Jan. 10, 2005 and entitled TISSUE REMOVER AND METHOD, U.S. Provisional Application No. 60/601,415, filed Aug. 13, 2004 and entitled DUAL PULSE-WIDTH MEDICAL LASER WITH PRESETS, U.S. Provisional Application No. 60/601,415, filed Sep. 17, 2004 and entitled LASER HANDPIECE ARCHITECTURE AND METHODS, and U.S. application Ser. No. 09/848,010, filed May 2, 2001 and entitled DERMATOLOGICAL CUTTING AND ABLATING DEVICE, the entire contents of all which are incorporated herein by reference. In some embodiments, the sensor may comprise one or more visual feedback implements. The visual feedback implement can be used, for example, (a) in a form that is integrated into a handpiece or output end of an electromagnetic energy output device, (b) in a form that is attached to the handpiece or electromagnetic energy output device, or (c) in conjunction with (e.g., not attached to) the handpiece or electromagnetic energy output device, wherein such handpieces and devices can facilitate cutting, ablating, treatments, and the like. Treatments can include low-level light treatments such as described in the above referenced U.S. Provisional Application No. 60/687,991 and U.S. Provisional Application No. 60/687,256, filed Jun. 3, 2005 and entitled TISSUE TREATMENT DEVICE AND METHOD, the entire contents of which are expressly incorporated herein by reference.

For example, one implementation may be useful for, among other things, optimizing, monitoring, or maximizing a cutting effect of an electromagnetic energy emitting device, such as a laser handpiece. The laser output can be directed, for example, into fluid (e.g., an air and/or water spray or an atomized distribution of fluid particles from a water connection and/or a spray connection near an output end of the handpiece) that is emitted from the handpiece above a target surface. An apparatus including corresponding structure for directing electromagnetic energy into an atomized distribution of fluid particles above a target surface is disclosed, for example, in the above-referenced U.S. Pat. No. 5,574,247. Large amounts of laser energy, for example, can be imparted into the fluid (e.g., atomized fluid particles), which can comprise water, to thereby expand the fluid (e.g., fluid particles) and apply disruptive (e.g., mechanical) cutting forces to the target surface. During a procedure, such as an oral procedure where access and visibility are limited, careful and close-up monitoring by way of a visual feedback implement of (a) interactions between the electromagnetic energy and the fluid (e.g., above the target surface) and/or (b) cutting, ablating, treating or other impartations of disruptive surfaces to the target surface, can improve a quality of the procedure.

In certain embodiments, visualization optical fibers (e.g., a coherent fiber bundle) can be provided that are configured to transmit light from the distal end D to the proximal end P, for routing images (e.g., working-surface images) acquired at or in a vicinity of the distal end by a visual feedback implement. According to some embodiments, the visual feedback implement can comprise an image-acquisition device (e.g., CCD or CMOS camera) for obtaining or processing images from the distal end D. The visual feedback implement can be built-in or attached (e.g., removably attached) to the handpiece and, further, can be disposed at various locations on or in connection with the handpiece between the proximal end P and distal end D, or proximally of the proximal end P. According to this and any of the other embodiments described herein, one or more of the optical fibers 16, 17, 18 and 20, and the visualization optical fibers (not shown), can be arranged, for example, outside of the handpiece envelope. A few applications for the presently-described visual feedback implement may include periodontal pockets (e.g., diagnostic and treatment), endodontics (e.g., visualization of canals), micro-dentistry, tunnel preparations, caries detection and treatment, bacteria visualization and treatment, general dentistry, and airborne-agent and gas detection applications as described in the above-referenced U.S. Provisional Application No. 60/688,109.

According to another embodiment of the present invention, electromagnetic radiation (e.g., one or more of blue light, white light, infrared light, a laser beam, reflected/scattered light, fluorescent light, and the like, in any combination) may be transmitted in one or both directions through one or more of the fibers 16, 17, 18, and 20, in any combination. Outgoing and incoming beams of electromagnetic radiation can be separated or split, for example, according to one or more characteristics thereof, at the proximal end P (FIG. 1) using a beam splitter, such as a wavelength-selective beam splitter (not shown), in a manner known to those skilled in the art.

Figure 7:
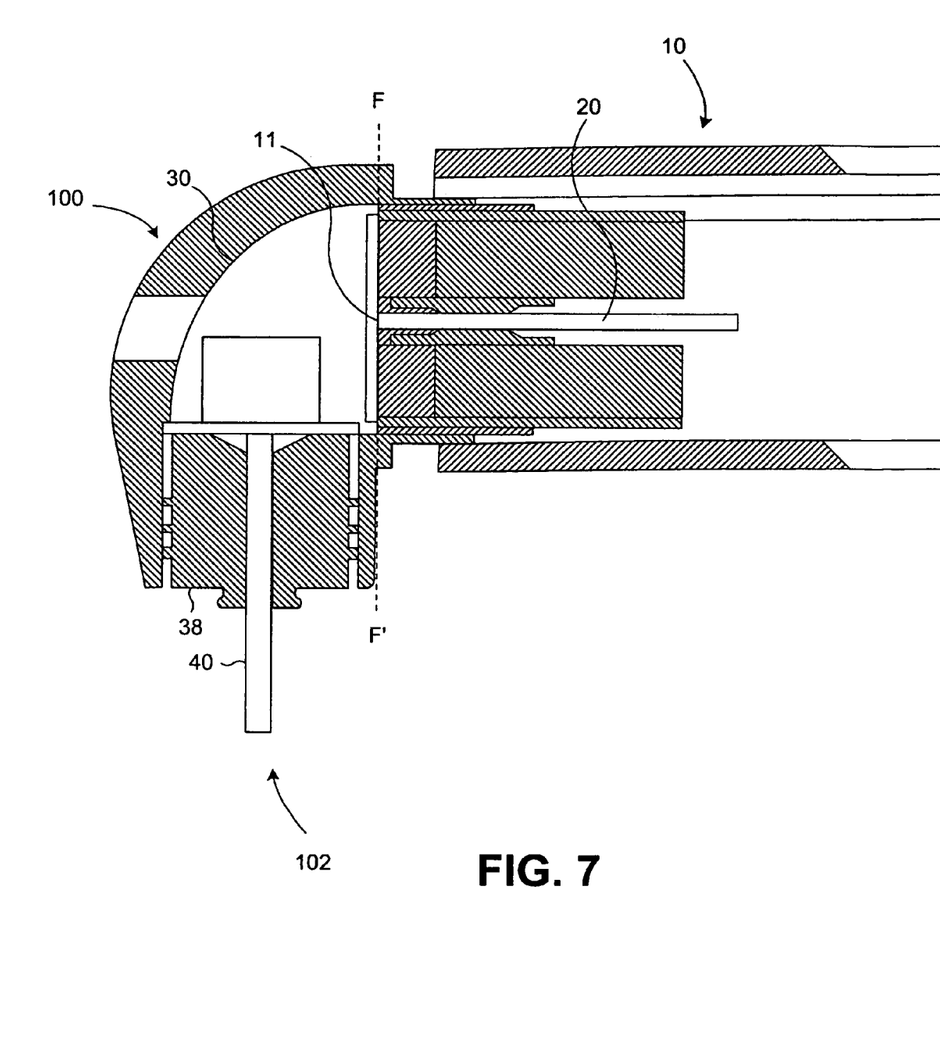
FIG. 7 is a cross-sectional view of an illumination device and a handpiece according to an example of the present invention.

In certain embodiments of the invention, illumination device 10, as shown, for example, in FIG. 1, may be useable in a person's hand or other suitable holding device to direct light toward a target surface. In other embodiments, the illumination device 10, which may comprise an optical fiber 20 oriented in a direction nominally parallel to a longitudinal axis of the illumination device 10, may be separate from but configured to be coupled to a handpiece 100 as illustrated in FIG. 7. Handpiece 100 (FIG. 7), which, in the illustrated embodiment, is structured to be held in a user's hand, can comprise a treatment output end 102 that is oriented at an angle relative to the longitudinal axis of the illumination device 10. Optical fiber 20 may terminate at an internal output end 1 coinciding with phantom line F-F', of illumination device 10 in the embodiment shown in FIG. 7. In the illustrated embodiment, treatment output end 102 is oriented at an approximately ninety degree angle to the longitudinal axis of illumination device 10. To direct the emitted light from fibers 18 and 20 toward treatment output end 102, a reflector 30 is provided with handpiece 100. An embodiment of reflector 30 can comprise a parabolic mirror as described in U.S. Pat. No. 6,389,193. In other embodiments, such as the embodiment of FIG. 2, reflector 30 may include a plurality of mirrors, such as first mirror 32 and second mirror 34. In still other embodiments, first and second mirrors 32 and 34 may comprise parabolic, toroidal, or flat surfaces. In additional embodiments, a fewer or greater number of mirrors may be provided.

Referring again to FIG. 2, first mirror 32 is illustrated as being configured to alter light emitted from optical fiber 20. In other words, as presently illustrated, first mirror 32 is configured to direct, for example, a beam 28 generated by a laser source from the internal output end 19 to the treatment output end 102. Second mirror 34, on the other hand, is illustrated as being configured to alter a path of light emitted from one or more of the fibers 16 and 17. In other words, mirror 34 can be configured to direct one or more beams of light, such as blue light or white light, from the internal output end 19 to the treatment output end 102. In addition, mirror 34 can be configured to direct light 64, which is reflected back from the target surface, toward fibers 18 (not visible in FIG. 2) for the provision of, for example, a signal that can be used for analysis, as described above. As depicted in FIG. 2, first reflector or mirror 32 overlaps or eclipses second reflector or mirror 34. Either or both of mirrors 32 and 34 may be removable and replaceable.

With continuing reference to FIG. 2, handpiece 100 is also illustrated as including a tip 40 to direct electromagnetic energy (e.g., light), as indicated by reference number 62, that is emitted from optical fiber 20 toward a target surface. In addition, a sleeve 38 may be provided with handpiece 100, wherein sleeve 38 may partially, substantially, or completely (e.g., wherein sleeve 38 comprises a ring or cylindrical shape) surround tip 40. As presently embodied, sleeve 38 can be constructed of a material that is substantially transparent to permit light 60 emitted from fibers 16 and/or 17, such as white light, to be directed to a target surface. Light 60 may be used, for example, to illuminate the target surface. The illumination or the intensity of illumination of the target surface may occur continuously during the procedure being performed, or may be interrupted. In addition, such illumination may be automatically or manually controlled. First and second mirrors 32 and 34 may also be constructed to focus one or more of the light beams into tip 40. In the illustrated embodiment, the first mirror 32 is constructed to focus the erbium laser beam emitted from optical fiber 20 into tip 40, and the second mirror 34 is constructed to focus the light emitted from fibers 16 and 17, such as blue light, white light, or other light, into sleeve 38. An embodiment of the handpiece 100 may comprise a plurality of LEDs (e.g., 2 or more, such as about 6 to 12, and in one implementation 10) concentrically disposed around the tip 40 in order to provide, according to certain implementations, one or more of a relatively bright, ultra-white and shadow-free illumination system that may significantly enhance maneuverability relative to, access to, and visibility of, a working surface. When employed in medical applications such as dental applications, any one or more of the above characteristics, such as enhanced illumination, may provide for significantly improved efficacy, accuracy and patient comfort.

Figure 5:
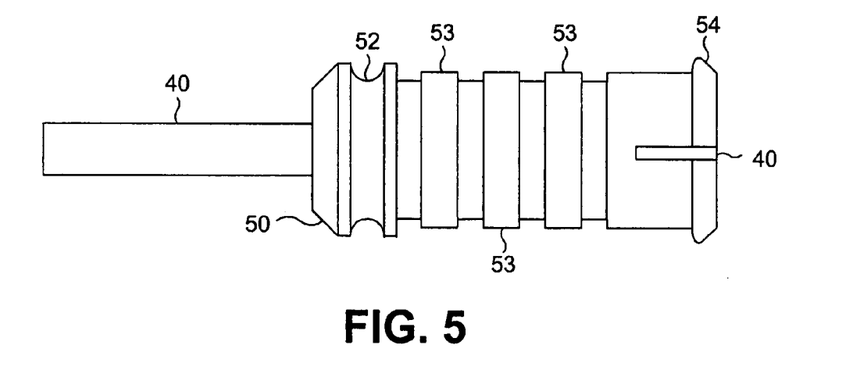
FIG. 5 is a side view of a combination formed by a fiber tip and a tip ferrule according to an example of the present invention.

In accordance with an aspect of the present invention, the tip 40 further may be surrounded by a tip ferrule 50. FIG. 5 is a magnified side elevation view showing a combination of the tip 40 and the tip ferrule 50. The tip ferrule 50 in the illustrated embodiment comprises a groove 52 that may be used to extract the tip ferrule 50 and, consequently, the tip 40 from the handpiece 100. The tip ferrule 50 in the illustrated embodiment further comprises a plurality of ring-shaped projections 53 (see also FIG. 2) that make contact with an interior of the sleeve 38 of the handpiece 100. Another embodiment of the tip ferrule 50 replaces the plurality of ring-shaped projections 53 with a plurality of O-rings. The tip ferrule 50 may have at least one locking shoulder 54 and, in certain embodiments, may have a plurality of locking shoulders. In the illustrated embodiment, the locking shoulder is capable of providing a "click" or "snap" feedback when the tip ferrule 50 is fitted into a recess 58 (FIG. 2), which recess is formed by structure of one or more of the treatment end 102, the handpiece 100 and the sleeve 38. In modified embodiments, a locking shoulder can be formed, instead, by structure of one or more of the treatment end, the handpiece and the sleeve; and a recess can be formed, instead, in the tip ferrule, so that the locking shoulder is capable of providing a "click" or "snap" feedback when the tip ferrule is fitted into the recess. The click or snap feedback can facilitate the securing or locking of the tip ferrule 50 to the handpiece 100. Thus, audible and/or tactile feedback in the form of a "click" or, in modified embodiments, other forms, can be provided to a user when an optical waveguide (e.g., tip 40), which is secured to the tip ferrule 50, is properly installed. As presently embodied, the tip 40 can be secured to the tip ferrule 40 by way of inserting an adhesive into a cavity 51 or gap disposed at a distal end of the tip ferrule 50, which cavity 51 is depicted in FIG. 2 as a distal portion of the tip ferrule 50 that surrounds but does not contact the tip 40.

Figure 6:
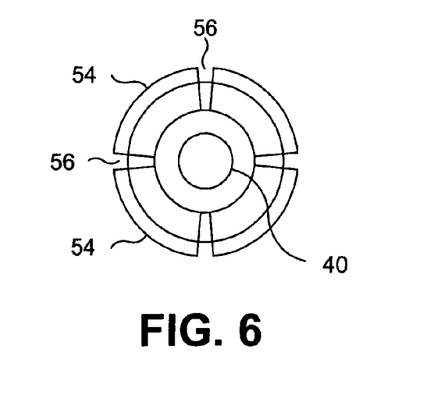
FIG. 6 is an on-axis top view of the fiber tip and tip ferrule combination of FIG. 5.

FIG. 6 is an on-axis top view of the tip ferrule 50 and tip 40 of FIG. 5. In the illustrated embodiment, the tip ferrule 50 comprises four locking shoulders capable of providing a "click" or "snap" feedback when the tip ferrule 50 is fitted into the recess 58 (FIG. 2). According to one implementation one or more gaps 56 disposed between locking shoulders may provide for a spring action capable, at least in part, of producing the click or snap feedback referred to above.

According to another aspect of the present invention, a facility may be provided for mixing spray air and spray water that may be directed toward a target surface. An illustration of an embodiment of a chamber for mixing spray air and spray water in the distal portion 24 of handpiece 100 is shown in FIG. 2a. A mixing chamber 80 (see also FIG. 2) comprises an air intake 83, which is connected to, for example, tubing (not shown) in the elongate body 12 that supplies spray air. Similarly, a water intake 84 receives fluid (e.g., water) from, for example, tubing (not shown) in the elongate body 12 that supplies water. The air intake 83 and the water intake 84, which may have circular cross-sections about 250 μm in diameter, join at an angle 82 that may approximate 110° in a typical embodiment. In certain embodiments, mixing may occur or begin to occur in a neighborhood where the air intake 83 and water intake 84 join, and a spray mixture 86 of water and air (e.g., particles or atomized particles) may be ejected through a fluid output 85. Fluid output 85 may have a circular cross-section measuring about 350 μm in diameter. A typical embodiment can comprise, for example, three such fluid outputs surrounding the tip 40 and tip ferrule 50 illustrated in FIG. 2. These fluid outputs may, for example, correspond to, comprise parts of, or comprise substantially all of, any of fluid outputs described in U.S. application Ser. No. 11/042,824, filed Jan. 24, 2005 and entitled ELECTROMAGNETICALLY INDUCED TREATMENT DEVICES AND METHODS, to the extent compatible, or, in other embodiments, structures described in the referenced provisional patent application may be modified to be compatible with the present invention.

Handpiece 100 may further include another tip structure 36, such as a curing tip, as illustrated in FIG. 2. Tip structure 36 can be coupled with tip 40 or, as presently embodied, can replace tip 40. In an embodiment wherein the tip structure 36 is coupled with tip 40, the tip structure 36 may comprise a hollow center for accommodating the tip 40 therethrough. In other embodiments, tip structure 36 can be coupled with or can replace both tip 40 and sleeve 38. In an embodiment wherein the tip structure 36 is coupled with tip 40 and sleeve 38, the tip structure 36 may abut against an output end of sleeve 38 and further may comprise a hollow center for accommodating the tip 40.

While the tip structure 36 in the illustrated embodiment comprises a cylindrical shape (e.g., a solid cylinder) that surrounds a space of tip 40, which space may or may not be occupied, other embodiments may comprise a tip structure that only partially surrounds the space (occupied or not) of tip 40. When tip structure 36 is a curing tip, the curing tip can be positioned in handpiece 100 and configured to receive or collect light (e.g., blue light) emitted from, for example, fibers 16 to direct the light toward a target surface and obtain a desired effect, such as curing of dental composites. To increase an amount of light that is collected by tip structure 36, a diameter can be chosen for tip structure 36 that will optimize or maximize a characteristic (e.g., an amount) of light collected. Tip 40 and tip structure 36 can be formed of a plastic-like material, including a plurality of plastic materials, that is/are optically transparent to permit the light to be effectively transmitted therethrough to and from a target surface.

In an exemplary implementation, illumination device 10 may have a total length of between about 1 and about 2 meters. In one particular embodiment, illumination device 10 can be about 1.6 meters long. Each proximal member 22A and 22B may have a diameter between about 2 millimeters (mm) and about 5 mm, such as about 3 mm. Typically, proximal members 22A, 22B, and 22C meet to define a unitary tubular structure having an outer diameter between about 4 mm and about 5 mm, such as about 4.5 mm (or about 3/16 of an inch). Proximal members 22A, 22B, and 22C may be arranged so that the fibers contained therein define a central lumen having a diameter ranging from about 1 mm to about 2 mm, such as about 1.5 mm (or about 1/16 of an inch). This central lumen can be structured to accommodate a power erbium laser fiber, such as optical fiber 20 capable of transmitting, for example, concentrated infrared electromagnetic energy. In the embodiment illustrated in FIG. 1, proximal members 22A, 22B, and 22C are routed together to form a unitary structure at a distance of approximately 5 centimeters (cm) from the proximal end P of elongate body 12. Power erbium optical fiber 20 may have a diameter of approximately 0.8 mm, and fibers 16 and, optionally, fibers 17, may have a diameter of about 1.5 mm. Fibers 18 may be about 0.5 mm in diameter. The internal output end 19 of illumination device 10 can include a substantially rigid, straight portion that is approximately 10 centimeters in length. Illumination device 10 can include six larger-diameter fibers, such as six fibers 16, or optionally can include three larger-diameter fibers 16 and three larger-diameter fibers 17 as shown in FIG. 3 concentrically arranged about a central lumen with six relatively smaller diameter fibers 18 concentrically arranged about the same central lumen. The numerical apertures of fibers 16 (and, optionally, fibers 17) and 18 can be about 0.68.

Light provided by two high power blue LEDs, which light may comprise visible electromagnetic energy relatively less concentrated than the infrared energy referred to above, may be directed into proximal members 22A and 22B to cure dental composites, whiten teeth, and/or detect dental caries. Each blue light LED can have a power of approximately ½ W. One suitable example of a high-power blue LED is a Luxeon Emitter, 5 W Dental, which emits light having a wavelength in a range of about 450 nm to about 470 nm with a bandwidth of about 20 nm (Model No. LXHL-PRD5). If illumination is desired at the target surface, two phosphoric filters can be placed in a light path between the blue light emitting LEDs and proximal members 22A and 22B. The phosphoric filters may be used as white-light shutters to provide white light to the target surface, as discussed above. The white light that is generated from filtering the blue light is typically reduced in power relative to the blue light. In the embodiment illustrated in FIG. 1, the white light is reduced to a range of about twenty percent to about thirty percent of the power of the blue light. Additional filters can be provided to alter the white light, as may be desired. In a preferred embodiment, a blue light filter is placed at the proximal end of each of the proximal members 22A and 22B. In other embodiments, however, the filters can be located at any location along the illumination device 10, including at the distal end.

By way of the disclosure herein, an illumination device has been described that utilizes electromagnetic energy to affect a target surface. In the case of dental procedures, the illumination device includes an optical fiber for transmitting laser energy to a target surface for treating (e.g., ablating) a dental structure, such as a tooth, a plurality of optical fibers for transmitting blue light for illumination, curing, whitening, and/or diagnostics of a tooth, a plurality of optical fibers for transmitting for example white light to a tooth to provide illumination of the target surface, and a plurality of optical fibers for transmitting light from the target surface back to a sensor for analysis. In the illustrated embodiment, the optical fibers that transmit blue light also transmit white light. In accordance with one aspect of the invention herein disclosed, an illumination device comprises an illumination tube having a feedback signal end and a double mirror handpiece.

In certain embodiments, the methods and apparatuses of the above embodiments can be configured and implemented for use, to the extent compatible and/or not mutually exclusive, with existing technologies including any of the above-referenced apparatuses and methods. Corresponding or related structure and methods described in the following patents assigned to BioLase Technology, Inc. are incorporated herein by reference in their entireties, wherein such incorporation includes corresponding or related structure (and modifications thereof) in the following patents which may be (i) operable with, (ii) modified by one skilled in the art to be operable with, and/or (iii) implemented/used with or in combination with any part(s) of, the present invention according to this disclosure, that/those of the patents, and the knowledge and judgment of one skilled in the art: U.S. Pat. Nos. 5,741,247; 5,785,521; 5,968,037; 6,086,367; 6,231,567; 6,254,597, 6,288,499; 6,350,123; 6,389,193; 6,544,256; 6,561,803; 6,567,582; 6,610,053; 6,616,447; 6,616,451; 6,669,685; and 6,744,790 all of which are commonly assigned and the entire contents of which are incorporated herein by reference.

For example, one implementation may be useful for tailoring, optimizing or maximizing an effect (e.g., cutting or ablating) of a laser. The laser output (e.g., from a power fiber) can be directed, for example, into fluid (e.g., an air and/or water spray or an atomized distribution of fluid particles from a water connection and/or a spray connection near the treatment output end 102) that is emitted from a fluid output of the handpiece 100 at the treatment output end 102 above a target surface (e.g., one or more of tooth, bone, cartilage and soft tissue). The fluid output may comprise a plurality of fluid outputs, concentrically arranged around a power fiber, as described in, for example, U.S. application Ser. No. 11/042,824 and U.S. Provisional Application No. 60/601,415. The power fiber may comprise, for example, optical fiber 20, and in various implementations may be coupled to an electromagnetic energy source comprising one or more of a wavelength within a range from about 2.69 to about 2.80 microns and a wavelength of about 2.94 microns. In certain implementations the power fiber may be coupled to one or more of an Er:YAG laser, an Er:YSGG laser, an Er, Cr:YSGG laser and a CTE:YAG laser, and in particular instances may be coupled to one of an Er, Cr:YSGG solid state laser having a wavelength of about 2.789 microns and an Er:YAG solid state laser having a wavelength of about 2.940 microns. An apparatus including corresponding structure for directing electromagnetic energy into an atomized distribution of fluid particles above a target surface is disclosed in the above-referenced U.S. Pat. No. 5,574,247. Large amounts of laser energy, for example, can be imparted into the fluid (e.g., atomized fluid particles), which can comprise water, to thereby expand the fluid (e.g., fluid particles) and apply disruptive (e.g., mechanical) cutting forces to the target surface.

The optical fibers and/or tip ferrules referred to herein may comprise plastic and/or be color coded to designate predetermined or predefined sizes, shapes or other properties. These materials may all be autoclavable. The tip ferrule and corresponding structure may comprise parts or substantially all of any of that described in U.S. Pat. No. 6,567,582, entitled FIBER TIP FLUID OUTPUT DEVICE, and in co-pending application entitled OUTPUT ATTACHMENTS CODED FOR USE WITH ELECTROMAGNETIC-ENERGY PROCEDURAL DEVICE to the extent compatible; or, in other embodiments, structures described in the referenced patents may be modified to be compatible with the device tip ferrule 50 disclosed in FIGS. 5 and 6.

While this invention has been described with respect to various specific examples and embodiments, it is to be understood that the invention is not limited thereto and that it can be variously practiced. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention should not be limited by the disclosed embodiments, but is to be defined by reference to the appended claims.

What is claimed is:

1. An apparatus, comprising:
an illumination device having a proximal end and a distal end, the illumination device being capable of transmitting concentrated infrared electromagnetic energy and relatively less-concentrated visible electromagnetic energy from the proximal end to the distal end, whereby the less-concentrated visible electromagnetic energy is concentrically disposed around the concentrated infrared electromagnetic energy;
a handpiece disposed at the distal end of the illumination device, the handpiece comprising (a) a treatment end connected to and disposed at an angle relative to the longitudinal axis of the illumination device, (b) a tip ferrule insertable into the treatment end, the tip ferrule comprising a distal end, and (c) a fiber tip insertable into the tip ferrule, the fiber tip being capable of receiving electromagnetic energy from the distal end of the illumination device, the handpiece being capable of receiving the concentrated infrared and less-concentrated visible electromagnetic energies from the distal end of the illumination device and of directing the electromagnetic energy to a target; and
a plurality of overlapping reflectors capable of directing electromagnetic energy from the distal end of the illumination device.

2. The apparatus as set forth in claim 1, wherein the tip ferrule comprises one or more locking shoulders capable of engaging a recess disposed in the treatment end, whereby insertion of the tip ferrule into the treatment end provides one or more of an audible feedback and a tactile feedback.

3. The apparatus as set forth in claim 1, wherein:

the tip ferrule surrounds a portion of the fiber tip, whereby the fiber tip extends outwardly from the distal end of the tip ferrule; and the tip ferrule is removable from the treatment end.

4. The apparatus as set forth in claim 3, wherein the fiber tip is secured within the tip ferrule by operation of a cavity formed in the distal end of the tip ferrule, the cavity surrounding but not contacting the fiber tip.

5. The apparatus as set forth in claim 4, wherein the fiber tip is secured by an adhesive disposed within the cavity.

6. The apparatus as set forth in claim 4, wherein the tip ferrule comprises one or more locking shoulders capable of engaging a recess disposed in the treatment end, whereby insertion of the tip ferrule into the treatment end provides one or more of an audible feedback and a tactile feedback.

7. The apparatus as set forth in claim 4, wherein the tip ferrule comprises a recess and the treatment end comprises one or more locking shoulders capable of engaging the recess, whereby insertion of the tip ferrule into the treatment end provides one or more of an audible feedback and a tactile feedback.

8. The apparatus as set forth in claim 1, wherein the tip ferrule comprises:
a groove at least partially surrounding the distal end of the tip ferrule, the groove being capable of facilitating removal of the tip ferrule from the treatment end; and
a plurality of ring-shaped projections, one or more of the ring-shaped projections being capable of establishing contact with an interior of the treatment end when the tip ferrule is inserted into the treatment end.

9. The apparatus as set forth in claim 1, wherein the illumination device comprises:
a first plurality of optical fibers capable of receiving the concentrated infrared and less-concentrated visible electromagnetic energies at the proximal end and of directing the received electromagnetic energies to the handpiece; and
a second plurality of optical fibers capable of receiving less-concentrated visible electromagnetic energy, which is reflected from a target back into the apparatus, from the handpiece and of directing the received less-concentrated visible electromagnetic energy to the proximal end of the illumination device.

10. The apparatus as set forth in claim 1, wherein during operation the handpiece is capable of rotating about an axis of the illumination device.

11. The apparatus as set forth in claim 10, wherein the handpiece comprises a plurality of reflectors capable of directing electromagnetic energy from the distal end of the illumination device to a target independent of an angle of rotation of the handpiece.

12. The illumination device as set forth in claim 1, and further comprising a fluid output that is configured to output fluid at the distal end.

13. The illumination device as set forth in claim 1, and further comprising a plurality of fluid outputs, concentrically arranged around a propagation path of the concentrated infrared electromagnetic energy and being configured to output fluid at the distal end.

14. The illumination device as set forth in claim 12, wherein the fluid output is configured to output fluid particles comprising water.

15. The illumination device as set forth in claim 12, wherein:
the fluid output comprises an atomizer configured to place atomized fluid particles into a volume above a target surface; and the concentrated infrared electromagnetic energy is output from the apparatus in such a way as to impart relatively large amounts of energy into the atomized fluid particles in the volume above the target surface to thereby expand the atomized fluid particles and impart disruptive forces onto the target surface.

16. An apparatus having a proximal end and a distal end holdable by a hand of a user, the apparatus comprising:
a treatment end having a sleeve disposed therein, the sleeve comprising a recess disposed on an inner surface thereof;
a tip ferrule disposed at least in part within the sleeve, the tip ferrule comprising a locking shoulder capable of engaging the recess;
a fiber tip, at least a portion of which is disposed within the tip ferrule, the fiber tip comprising a configuration for outputting first electromagnetic radiation of a first characteristic, whereby the apparatus is configured to output second electromagnetic radiation having a different characteristic and concentrically disposed around the first electromagnetic radiation; and
a plurality of overlapping reflectors capable of directing the first and second electromagnetic radiations along a path for emission from the distal end of the apparatus.

17. The apparatus as set forth in claim 16, wherein the apparatus comprises a handpiece disposed in a vicinity of an output end of a device.

18. The apparatus as set forth in claim 17, wherein the device is an illumination device.

19. The apparatus as set forth in claim 16, wherein engagement of the locking shoulder with the recess occurs when the tip ferrule is inserted into the sleeve and provides one or more of an audible feedback and tactile feedback.

20. The apparatus as set forth in claim 19, wherein the tip ferrule comprises a plurality of locking shoulders capable of engaging the recess and of providing at least one of an audible and tactile feedback when the tip ferrule is inserted into the sleeve and the recess is engaged.

21. The apparatus as set forth in claim 16, wherein:
the sleeve comprises a locking shoulder disposed on an inner surface thereof; and
the tip ferrule comprises a recess capable of being engaged by the locking shoulder whereby one or more of an audible feedback and a tactile feedback are generated.

22. The apparatus as set forth in claim 21, wherein the inner surface of the sleeve comprises a plurality of locking shoulders and the one or more audible and tactile feedbacks are generated when the tip ferrule is inserted into the sleeve.

23. The apparatus as set forth in claim 16, wherein:
at least a portion of the fiber tip is secured within the tip ferrule by an adhesive;
the tip ferrule comprises a distal end; and
at least a portion of the fiber tip extends outward from the distal end of the tip ferrule.

24. The apparatus as set forth in claim 23, wherein the tip ferrule is removable from the sleeve.

25. The apparatus as set forth in claim 24, wherein:
the sleeve comprises a recess disposed on an inner surface thereof; and
the tip ferrule comprises a plurality of locking shoulders, at least one of the locking shoulders being capable of engaging the recess and of providing one or more of an audible feedback and a tactile feedback when the tip ferrule is inserted into the sleeve and the recess is engaged.

26. The apparatus as set forth in claim 16, wherein the tip ferrule is color coded according to a function of the fiber tip.

27. The illumination device as set forth in claim 1, wherein the concentrated infrared electromagnetic energy is supplied from at least one of an Er:YAG laser, an Er:YSGG laser, an Er, Cr:YSGG laser and a CTE:YAG laser.

28. The illumination device as set forth in claim 1, wherein the target surface comprises one of tooth, bone, cartilage and soft tissue.

29. The apparatus as set forth in claim 16, wherein a first one of the plurality of reflectors is at least partially eclipsed by a second one of the plurality of reflectors, relative to a direction of propagation of electromagnetic energy to the first one of the plurality of reflectors.

30. An apparatus, comprising:
   an illumination device having a proximal end and a distal end, the illumination device being capable of transmitting concentrated infrared electromagnetic energy and relatively less-concentrated visible electromagnetic energy from the proximal end to the distal end, whereby the less-concentrated visible electromagnetic energy is concentrically disposed around the concentrated infrared electromagnetic energy;
   a handpiece disposed at the distal end of the illumination device, the handpiece being capable of receiving the concentrated infrared and less-concentrated visible electromagnetic energies from the distal end of the illumination device and of directing the electromagnetic energy to a target; and
   a plurality of overlapping reflectors capable of directing electromagnetic energy from the distal end of the illumination device, wherein a first one of the plurality of reflectors is at least partially eclipsed by a second one of the plurality of reflectors, relative to a direction of propagation of electromagnetic energy to the first one of the plurality of reflectors.

31. The apparatus as set forth in claim 30, and further characterized by the first reflector being capable of receiving the concentrated electromagnetic energy from an electromagnetic energy conduit and directing the concentrated electromagnetic energy to a fiber tip of the handpiece, the fiber tip directing the visible electromagnetic energy away from the handpiece; and the second reflector being capable of receiving the visible electromagnetic energy from one or more conduits and directing the visible electromagnetic energy to one or more tip waveguides of the handpiece, the one or more tip waveguides directing the visible electromagnetic energy away from the handpiece.

32. The apparatus as set forth in claim 29, wherein:
   the first one of the plurality of reflectors is capable of receiving the first electromagnetic energy from an electromagnetic energy conduit and directing the first electromagnetic energy to an output fiber tip, the output fiber tip directing the first electromagnetic energy away from the apparatus; and
   the second one of the plurality of reflectors is capable of receiving the second electromagnetic energy from one or more conduits and directing the second electromagnetic energy to one or more tip waveguides of the handpiece, the one or more tip waveguides directing the second electromagnetic energy away from the handpiece.

* * * * *